United States Patent
Rizoiu et al.

(10) Patent No.: US 7,261,558 B2
(45) Date of Patent: *Aug. 28, 2007

(54) ELECTROMAGNETIC RADIATION EMITTING TOOTHBRUSH AND DENTIFRICE SYSTEM

(75) Inventors: Ioana M. Rizoiu, San Clemente, CA (US); Andrew I. Kimmel, San Clemente, CA (US)

(73) Assignee: Biolase Technology, Inc., Irvine, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 10/624,963

(22) Filed: Jul. 21, 2003

(65) Prior Publication Data

US 2004/0091834 A1 May 13, 2004

Related U.S. Application Data

(63) Continuation of application No. 09/445,947, filed as application No. PCT/US98/12836 on Jun. 19, 1998, now Pat. No. 6,616,451.

(60) Provisional application No. 60/050,343, filed on Jun. 20, 1997.

(51) Int. Cl.
*A61C 3/00* (2006.01)
(52) U.S. Cl. .......................... 433/29; 433/216
(58) Field of Classification Search ............. 433/29, 433/215, 216; 362/109
See application file for complete search history.

(56) References Cited

U.S. PATENT DOCUMENTS 407,115 A 7/1889 Pratt (Continued)

FOREIGN PATENT DOCUMENTS

DE 296 21 445 * 4/1997

(Continued)

OTHER PUBLICATIONS

International Preliminary Examination Report, Mar. 15, 2000, PCT/US98/12836.

(Continued)

*Primary Examiner*—Ralph A. Lewis
(74) *Attorney, Agent, or Firm*—Stout, Uxa, Buyan & Mullins, LLP (57) ABSTRACT

A cleaning and whitening system for teeth having an electromagnetic radiation emitting toothbrush and a dentifrice with a photosensitive agent is disclosed. The toothbrush has a cleaning surface, such as bristles. The toothbrush is also adapted to direct electromagnetic radiation toward the cleaning surface. The electromagnetic radiation may be monochromatic or polychromatic. Further, the electromagnetic radiation may be substantially free of ultraviolet radiation. Additionally, the electromagnetic radiation may consist essentially of wavelengths within a range of 300 to 750 nanometers. The photosensitive agent is dispersed throughout the dentifrice. The dentifrice transmits the electromagnetic radiation through a varying thickness disposed over a target surface during use of the system. As a result, a significant portion of the photosensitive agent reacts, resulting in whitening stains, removing and/or disclosing undesired substances, and/or foaming. The dentifrice may be clear and may have clear abrasive particles. A method for tuning the cleaning and whitening system for teeth includes formulating the dentifrice with photosensitive agents that react to a range of electromagnetic radiation and providing a toothbrush that emits that electromagnetic radiation range. Another method of tuning the cleaning and whitening system includes designing a toothbrush that emits a range of electromagnetic radiation and formulating a dentifrice with photosensitive agents that react to the electromagnetic radiation range.

147 Claims, 2 Drawing Sheets

U.S. PATENT DOCUMENTS

| | | | |
|---|---|---|---|
| 2,834,344 A | 5/1958 | Kanai | |
| 3,261,978 A | 7/1966 | Brenman | |
| 3,478,741 A | 11/1969 | Simor | |
| 3,520,297 A | 7/1970 | Bechtold | |
| 3,667,454 A * | 6/1972 | Prince | 601/18 |
| 4,273,535 A | 6/1981 | Yamamoto et al. | |
| 4,502,497 A | 3/1985 | Siahou | |
| 4,661,070 A * | 4/1987 | Friedman | 433/203.1 |
| 4,779,173 A * | 10/1988 | Carr et al. | 362/109 |
| 4,877,401 A | 10/1989 | Higuchi et al. | |
| 4,952,143 A * | 8/1990 | Becker et al. | 433/32 |
| 4,969,868 A | 11/1990 | Wang | |
| 4,983,381 A | 1/1991 | Torres Zaragoza | |
| 5,003,434 A * | 3/1991 | Gonser et al. | 362/572 |
| 5,030,090 A * | 7/1991 | Maeda et al. | 433/29 |
| 5,030,093 A | 7/1991 | Mitnick | |
| 5,032,178 A * | 7/1991 | Cornell | 106/35 |
| 5,055,048 A | 10/1991 | Vassiliadis et al. | |
| 5,094,619 A | 3/1992 | McLaughlin | |
| 5,160,194 A * | 11/1992 | Feldman | 362/109 |
| 5,306,143 A | 4/1994 | Levy | 433/29 |
| 5,611,793 A | 3/1997 | Wilson et al. | |
| 5,645,428 A * | 7/1997 | Yarborough | 433/215 |
| 5,658,148 A * | 8/1997 | Neuberger et al. | 433/215 |
| 5,813,855 A * | 9/1998 | Crisio, Jr. | 433/29 |
| 5,879,159 A * | 3/1999 | Cipolla | 433/29 |
| 5,894,620 A * | 4/1999 | Polaert et al. | 15/22.1 |
| 6,026,828 A * | 2/2000 | Altshuler | 132/311 |
| 6,056,548 A * | 5/2000 | Neuberger et al. | 433/215 |
| 6,089,740 A | 7/2000 | Forehand et al. | |
| 6,202,242 B1 | 3/2001 | Salmon et al. | |
| 6,290,496 B1 * | 9/2001 | Azar et al. | 433/29 |
| 6,616,451 B1 * | 9/2003 | Rizolu et al. | 433/215 |
| 6,862,771 B1 | 3/2005 | Muller | |
| 2003/0232303 A1 | 12/2003 | Black | |
| 2004/0006332 A1 | 1/2004 | Black | |
| 2004/0091834 A1 | 5/2004 | Rizoiu et al. | |
| 2004/0191729 A1 | 9/2004 | Altshuler et al. | |
| 2004/0193235 A1 | 9/2004 | Altshuler et al. | |
| 2004/0193236 A1 | 9/2004 | Altshuler et al. | |
| 2004/0204745 A1 | 10/2004 | Altshuler et al. | |
| 2004/0210276 A1 | 10/2004 | Altshuler et al. | |
| 2005/0050658 A1 | 3/2005 | Chan et al. | |
| 2005/0050659 A1 | 3/2005 | Chan et al. | |
| 2005/0053895 A1 | 3/2005 | Pinyayev et al. | |
| 2005/0053896 A1 | 3/2005 | Pinyayev et al. | |
| 2005/0053898 A1 | 3/2005 | Ghosh et al. | |

FOREIGN PATENT DOCUMENTS

| | | | |
|---|---|---|---|
| EP | 0 406 454 | | 1/1991 |
| WO | WO92/06671 | * | 4/1992 |
| WO | WO93/09847 | | 5/1993 |
| WO | WO94/09850 A | | 5/1994 |
| WO | WO97/01298 | * | 1/1997 |
| WO | WO98/10711 A | | 3/1998 |

OTHER PUBLICATIONS

International Search Report, Dec. 30, 1998, PCT/US98/12836.
European Search Report, Jul. 15, 2005, EP 98 93 1410.

* cited by examiner

ELECTROMAGNETIC RADIATION EMITTING TOOTHBRUSH AND DENTIFRICE SYSTEM

PRIORITY INFORMATION

This application is a continuation of application Ser. No. 09/445,947 filed Aug. 29, 2000 and now U.S. Pat. No. 6,616,451, entitled ELECTROMAGNETIC RADIATION EMITTING TOOTHBRUSH AND DENTIFRICE SYSTEM, which issued on Sep. 9, 2003 which is a 371 of PCT/US98/12836 filed Jun. 19, 1998, and which claims the benefit of U.S. Provisional Application No. 60/050,343, filed on Jun. 20, 1997, which are commonly assigned and the contents of which are expressly incorporated herein by reference.

BACKGROUND OF THE INVENTION

1. Field of the Invention

This invention relates to generally to dental hygiene and, more particularly, to toothbrush and brushing compound combinations.

2. Description of Related Art

Proper dental hygiene is not only important for dental health reasons, but for personal appearance considerations as well. One of the many techniques people employ to improve their personal appearance through dental hygiene is to have their teeth whitened. Teeth whitening techniques vary in cost, convenience, and effectiveness.

Dental health professionals use many techniques to whiten teeth to improve their patients' personal appearance. High pressure baking soda solutions are used to scour teeth in a process analogous to sand-blasting. Chemical treatments abound for bleaching the teeth. However, these treatments require the inconvenience of visiting a dental health practice and the expense involved in having the treatment performed by a dental health professional.

Brushing with a dentifrice, whether a toothpaste, gel, cream, or powder, has some effect in whitening teeth due to the abrasive action of the dentifrice on the teeth. A relatively simple method of whitening teeth comprises brushing them with a dentifrice comprising whitening agents. Hydrogen peroxide, a common whitening agent, is a component in many off-the-shelf toothpastes and tooth gels. However, certain diets and activities, such as smoking, stain the teeth beyond the ability of a dentifrice alone to sufficiently whiten them.

The prior art discloses toothbrushes equipped with a light source that can illuminate the brushing region and provide beneficial radiation to the tooth surface. Examples of illuminating toothbrushes are disclosed in U.S. Pat. No. 5,306,143 entitled DENTAL HYGIENE APPLIANCE; U.S. Pat. No. 5,160,194 entitled TOOTHBRUSH WITH EXTERNALLY ILLUMINATED BRISTLES; U.S. Pat. No. 5,030,090 entitled OPTICAL TOOTHBRUSH AND METHOD OF USE; and U.S. Pat. No. 4,779,173 entitled ILLUMINATED BRUSH DEVICE, all of which are expressly incorporated herein by reference in their entireties.

A need exists for an improvement in whitening and cleaning teeth which does not require visiting a dental health professional and which improves the whitening of prior art dentifrices and electromagnetic radiation emitting toothbrushes.

SUMMARY OF THE INVENTION

A cleaning and whitening system for teeth having an electromagnetic radiation emitting toothbrush and a dentifrice with a photosensitive agent is disclosed. The toothbrush has a cleaning surface, such as bristles. The toothbrush is also adapted to direct electromagnetic radiation toward the cleaning surface. The electromagnetic radiation may be monochromatic or polychromatic. Further, the electromagnetic radiation may be substantially free of ultraviolet radiation. Additionally, the electromagnetic radiation may consist essentially of wavelengths within a range of 300 to 750 nanometers. The photosensitive agent is dispersed throughout the dentifrice. The dentifrice transmits the electromagnetic radiation through a varying thickness of dentifrice disposed over a target surface during use of the system. As a result, a significant portion of the photosensitive agent reacts, resulting in whitening stains, removing and/or disclosing undesirable substances, and/or foaming. The dentifrice may be clear and may have clear abrasive particles.

In an aspect of the invention, the cleaning and whitening system for teeth comprises a toothbrush having a cleaning surface, the toothbrush being adapted to direct polychromatic electromagnetic radiation toward the cleaning surface, wherein the polychromatic electromagnetic radiation consists essentially of wavelengths within a range of 300 to 750 nanometers.

In an aspect of the invention, the teeth cleaning and whitening system comprises a dentifrice that has a photosensitive agent that reacts substantially only to electromagnetic radiation within a predetermined range. The system further comprises a toothbrush having a cleaning surface, the toothbrush being adapted to direct electromagnetic radiation toward the cleaning surface, wherein the electromagnetic radiation is bound to wavelengths that are substantially within the predetermined range.

In a further embodiment of the invention, the photosensitive agent has a relatively high reaction rate when exposed to electromagnetic radiation in a highly reactive portion of the predetermined range compared to an average reaction rate when the photosensitive agent is exposed to electromagnetic radiation over the predetermined range. Additionally, the polychromatic electromagnetic radiation emitted by the toothbrush is bound to wavelengths that are substantially within the highly reactive portion of the predetermined range.

In an aspect of the invention, a method of tuning the cleaning and whitening system for teeth includes a step of formulating the dentifrice with photosensitive agents that react to a range of electromagnetic radiation, and a step of providing a toothbrush that emits that electromagnetic radiation range.

In another aspect of the invention, a method of tuning the cleaning and whitening system includes a step of designing a toothbrush that emits a range of electromagnetic radiation and another step of formulating a dentifrice with a photosensitive agent that reacts to the electromagnetic radiation range.

DETAILED DESCRIPTION OF THE PRESENTLY PREFERRED EMBODIMENTS

Figure 1:
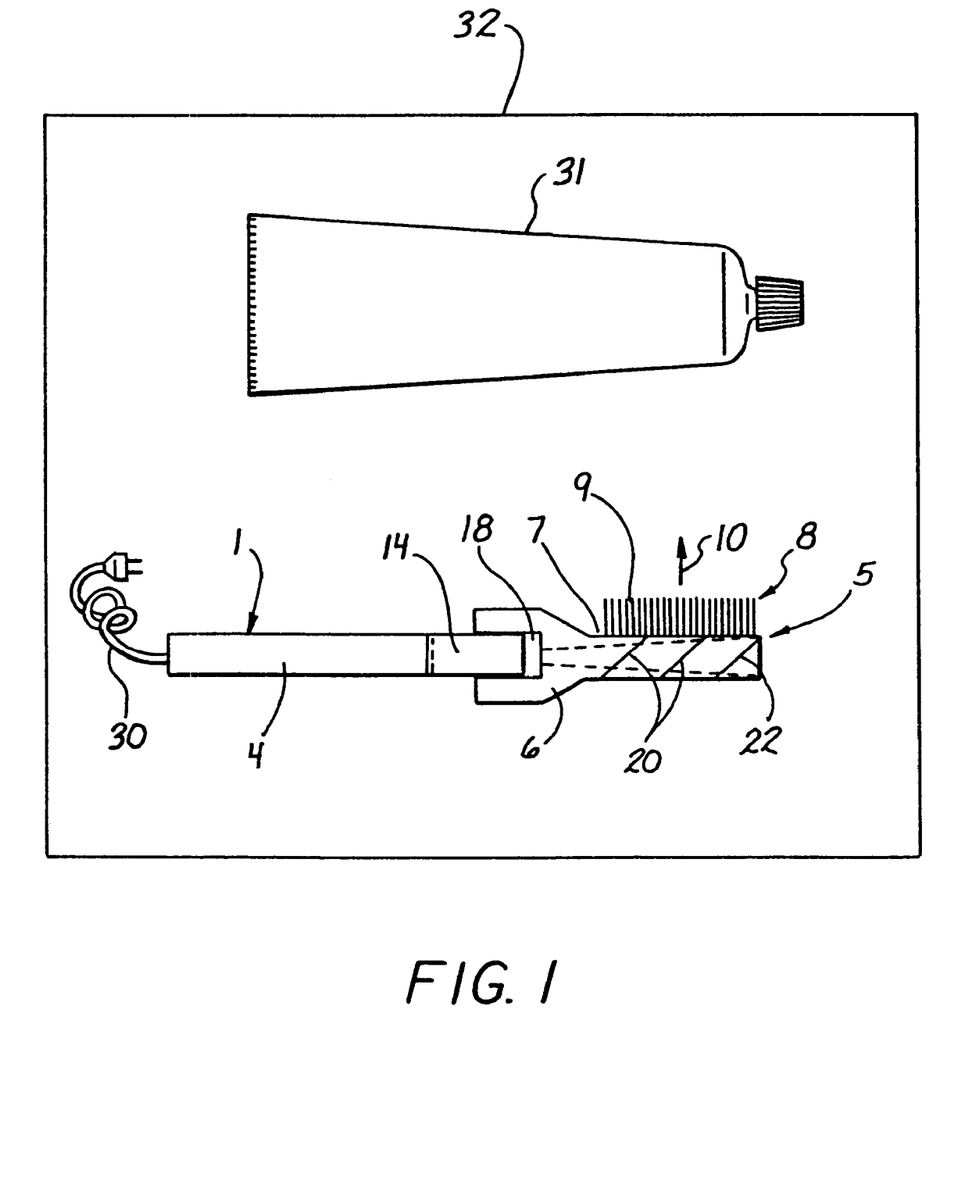
FIG. 1 is a schematic view of an electromagnetic radiation emitting toothbrush and a container of brushing compound in a package according to an embodiment of the invention.

Referring now to FIG. 1, an electromagnetic radiation emitting toothbrush 1 and a container 31 of brushing compound are shown disposed within a package 32. Other embodiments of the invention have differing designs of the container 31. Tile package 32 is shown schematically and embodiments of the invention may use any suitable package design and configuration.

The general structure of the toothbrush 1 is disclosed in U.S. Pat. No. 5,306,143 entitled DENTAL HYGIENE APPLIANCE to Levy, the contents of which are incorporated herein by reference. Modified embodiments of the invention may use other suitable electromagnetic radiation emitting toothbrushes. The basic components of the toothbrush 1 include a handle 4 and a brushing head 5. The brushing head 5 is constituted by a body 6 having a base surface 7 from which a set of tooth brushing bristles 8 project. The composition and form of the bristles 8, and the manner in which the bristles 8 are secured to the body 6, conform to conventional practice in the toothbrush art. The ends 9 of the bristles 8 comprise a cleaning surface that is used for scouring teeth and alike. Other embodiments of the invention may have other types of cleaning surfaces, such as, for example, a sponge or other type of foam.

The toothbrush 1 is further provided with means for directing monochromatic radiation of a selected type from the body 6 in the direction of an arrow 10, which is generally parallel to the direction in which the bristles 8 project from the body 6. The radiation is emitted generally via the base surface 7 of the body 6. In modified embodiments of the invention, the radiation may be emitted from the handle 4, guided by the bristles 8, or any other suitable means for directing radiation to the ends 9 of the bristles, which form the cleaning surface of the illustrated embodiment of the invention.

The handle 4 is provided with a light-emitting device 14 for generating the electromagnetic radiation. Embodiments of the invention may use any suitable means for generating the electromagnetic radiation, such as a semiconductor laser that generates monochromatic electromagnetic radiation or a light emitting diode that emits polychromatic electromagnetic radiation.

The brushing head 5 is shown having a lens 18, one or more semitransparent mirrors 20 and a fully reflecting mirror 22. In the illustrated embodiment of the invention, the electromagnetic radiation produced by light-emitting device 14 is in the form of a small diameter collimated beam extended along an axis corresponding to the longitudinal axis of the handle 4 and the head 5. The mirrors 20 and 22 are oriented at an angle of 45° to the beam axis, and the lens 18 is constructed and arranged to give the electromagnetic radiation beam a slightly diverging form such that the beam will diverge to an area essentially coextensive with the area occupied by the mirror 22. Modified embodiments of the invention may use other arrangements for directing the electromagnetic radiation generating means to the cleaning surface of the brushing head 5.

The body 6 may itself be made of a plastic which is transparent to the electromagnetic radiation so that portions of the radiation are reflected in the direction 10 by the mirrors 20, and the remaining radiation is reflected by the mirror 22. The optical system constituted by the lens 18 and the mirrors 20, 22 is arranged to cause radiation to traverse an area, which is at least approximately coextensive with the area covered by the ends 9 of the bristles 8. However, the radiation area may, depending on the particular operations to be performed, extend over a smaller or larger cleaning surface. Modified embodiments of the invention may use other optical system arrangements.

Figure 2:
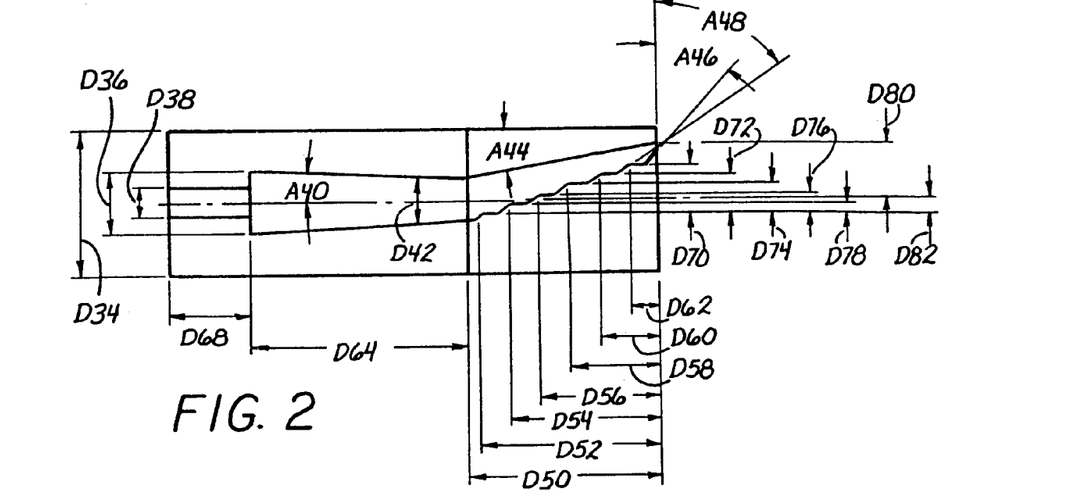
FIGS. 2-4 are schematic views of an electromagnetic radiation emitting toothbrush according to another embodiment of the invention.
Figures 3, 4:
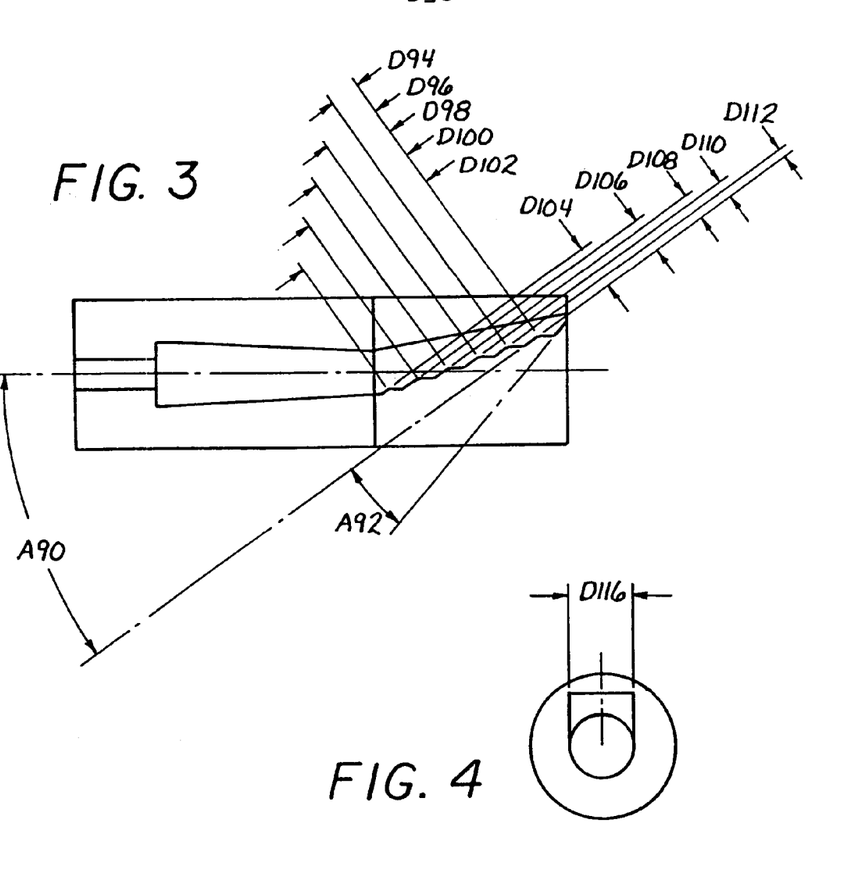

A modified embodiment is illustrated in FIGS. 2-4. The mirrors 20, 22 are replaced with reflective surfaces. The reflective surfaces can be formed on the interior surfaces of the outer, stepped portion of the head of the toothbrush. The reflective surfaces may comprise foil or foils, for example, which are embedded into the plastic and wrapped, for example, around the back and sides of the stepped portion of the head. Other materials and/or types of reflective surfaces may be used to increase, decrease, and/or change a distribution of radiation transmitted through the bristles.

In FIG. 2, the head tapers from a diameter of 0.440 units, to a diameter of 0.287 units just before the stepped portion. This diameter, which is just before the stepped portion, can be increased to facilitate greater transmission of radiation to the stepped portion or, in other embodiments, can be decreased to attenuate an amount of radiation transmitted to the stepped portion. A width of the head, which is 0.430 units as shown in FIG. 4, may similarly be increased to facilitate greater transmission of radiation through the bristles or, in other embodiments, may be decreased to attenuate an amount of radiation transmitted through the bristles. The number, angles, sizes, etc. of the steps forming the reflective surfaces may be changed to increase, decrease, and/or change a distribution of radiation through the bristles. In FIG. 2, the distance D34 is 1.000 units, the distance D36 is 0.440, the distance D38 is 0.200, the angle A40 is 3 degrees, the distance D42 is 0.287, the angle A44 is 10 degrees, the angle A46 is 40 degrees, and the angle A48 is 55 degrees. The distance D50 is 1.295 units, the distance D52 is 1.210, the distance D54 is 1.006, the distance D56 is 0.803, the distance D58 is 0.599, the distance D60 is 0.395, the distance D62 is 0.192, the distance D70 is 0.335, the distance D72 is 0.268, the distance D74 is 0.201, the distance D76 is 0.134, the distance D78 is 0.067, the distance D80 is 0.383 and the distance D82 is 0.100. In FIG. 3, the angle A90 is 35 degrees, the angle A92 is 15 degrees, the distance D94 is 0.205 units, the distance D96 is 0.411, the distance D98 is 0.616, the distance D100 is 0.821, the distance D102 is 1.026, the distance D104 is 0.310, the distance D106 is 0.248, the distance D108 is 0.186, the distance D110 is 0.124 and the distance D112 is 1.062. In FIG. 4, the distance D116 is 0.430 units.

In other embodiments of the invention prior art toothbrushes equipped with a light source, which illuminates the brushing region and which provides beneficial radiation to the tooth surface, call be used. Examples of illuminating toothbrushes are disclosed in U.S. Pat. No. 5,306,143 entitled DENTAL HYGIENE APPLIANCE; U.S. Pat. No. 5,160,194 entitled TOOTHBRUSH WITH EXTERNALLY ILLUMINATED BRISTLES; U.S. Pat. No. 5,030,090 entitled OPTICAL TOOTHBRUSH AND METHOD OF USE; and U.S. Pat. No. 4,779,173 entitled ILLUMINATED BRUSH DEVICE, all of which are expressed incorporated herein by reference in their entireties.

The handle 4 includes a power cord 30 which may be plugged into a wall outlet in order to supply operating power to the light-emitting device 14. Other embodiments of the invention may have a replaceable or rechargeable battery in the handle 4 as the power source for the light-emitting device 14. In addition, in the illustrated embodiment, brushing head 5 is readily detachable from handle 4. This allows for a plurality of brushing heads 5, each used by a different individual, to be mounted on handle 4 for use. Additionally, lens 18 may form a unit with handle 4, so that each of the brushing heads 5 need not be provided with its own lens. This configuration would reduce the cost associated with manufacturing each head 5. Modified embodiments of the invention may have the electromagnetic radiation supplied from a source external to the toothbrush 1 via a fiber-optic cable, as is known to those skilled in the art.

In one embodiment, the toothbrush 1 emits polychromatic electromagnetic radiation of a wavelength and an intensity for facilitating the removal of undesired substances from a target surface. Typical undesired substances include bacteria, plaque, tartar, and calculus, all of which contribute to, or are precursors of, tooth decay. In other embodiments of the invention monochromatic electromagnetic radiation is emitted to accomplish similar objectives.

The dentifrice is formulated in one embodiment to comprise photosensitive agents that assist in removing undesired substances from teeth, such as stains, bacteria, plaque, tartar, and calculus. The photosensitive agents react to the emitted electromagnetic radiation of the toothbrush during brushing to enhance removal of the undesired substances.

The removal enhancement provided by the dentifrice may be direct, such as when the photosensitive agent reacts to the electromagnetic radiation and, in turn, reacts with the undesired substance to remove it. Examples of materials that may comprise a photosensitive agent include peroxy compounds, salt compounds, anti-bacteria agents, and anti-plaque agents. The salt compounds may or may not be dissolved in the dentifrice. The use of peroxide compounds, such as hydrogen peroxide and carbamide peroxide, in dentifrices is known in the art, as disclosed in U.S. Pat. No. 4,990,089 entitle METHOD AND MATERIAL FOR BRIGHTENING TEETH, which is incorporated herein by reference in its entirety. In accordance with the present invention, the electromagnetic radiation emitted by the toothbrush 1 during brushing enhances tile whitening and cleaning of the teeth when used in combination with the dentifrice comprising a photosensitive agent.

Other embodiments of the invention comprise dentifrices used in connection with a photosensitive agent comprising a foaming agent. The foaming agent generates foam in the presence of the electromagnetic radiation. The foam operates as a carrier that delivers dentifrice to areas not reachable by the toothbrush cleaning surface, thus improving the overall cleaning and whitening of the teeth. The foaming agent may comprise a peroxy compound in one embodiment of the invention.

In addition, when certain photosensitive agents are brought into contact with one or more of the undesired substances, the application of electromagnetic radiation having an appropriate wavelength and energy content can render the substance or substances visible.

By way of example, one of the purposes of tooth brushing is to remove bacteria which have collected on tooth surfaces, frequently in pits and fissures in the tooth enamel. It is known that regardless of the care exercised and time spent in a brushing session, some of the bacteria deposits may not be dislodged and removed from the tooth surfaces. It is also known that there are chemical products, known as disclosing solutions, which can make any deposited bacteria visible. There are other photosensitive agents, which may be preferable to the conventional disclosing solutions, which will react with bacteria in such a manner as to render the bacteria visible in the presence of radiation having a certain wavelength or wavelengths.

When such a dentifrice is employed, the photosensitive agent comprises a disclosing agent that renders any existing bacteria visible under the radiation produced by the light-emitting device 14 by changing the color of the disclosing agent. The disclosing agent has an affinity for undesired substances, such as bacteria and/or plaque, resulting in the disclosing agent being concentrated about the undesired substances relative to other areas on the target surface. As a result, the radiated, disclosing agent announces locations of undesired substances on the teeth surface, so that brushing can be continued until the user observes that all bacteria have been removed from all visible tooth surfaces. While it would be more difficult to carry out this procedure on lingual tooth surfaces, this would be possible, if brushing were carried out while viewing those surfaces with a mirror. The dentifrices of modified embodiments of the invention may visually announce plaque and/or other undesired substances during brushing as well.

According to one exemplary embodiment of the invention, the chemical product consists of or contains Black Shade No. 4625, which can be obtained by Crompton & Knowles, Ingredient Technology Division, of Reading, Pa. In this embodiment, the radiation source produces radiation at a wavelength, or wavelengths, of between 0.8 µm and 1 µm. As presently embodied, the radiation source produces polychromatic electromagnetic radiation of wavelengths ranging from 0.8 µm to 1 µm. In a modified embodiment of the invention, the radiation source produces polychromatic electromagnetic radiation of wavelengths comprising at least a portion of the different wavelengths in the 0.8 µm to 1 µm range. In still another modified embodiment, the radiation source produces electromagnetic radiation of a single wavelength in the 0.8 µm to 1 µm range. The radiation source may comprise, for example, a Nd:YAG laser.

The source is adjusted to emit radiation at an energy level selected on the basis of the expected concentration of the Black Shade No. 4625 in the material to be treated. The Black Shade No. 4625 will stain, for example, cariogenic bacteria or streptococcus faecalis black so that this bacteria, or any other substance absorbing Black Shade No. 4625, will readily absorb the laser radiation. As an alternative to the Black Shade No. 4625 in the example, any other substance for staining the bacteria, for example, black can be used. Other photosensitive substances may be used in addition to, or as an alternative to, black. Agents comprising oranges, reds, browns, yellows, greens, blues, etc., supplied, for example, by Crompton & Knowles, Ingredient Technology Division, of Reading, Pa., may be selected, along with radiation sources having corresponding wavelengths. According to one specific embodiment, the chemical product is sudan red as a vital stain when the radiation source is an argon laser.

The radiation energy density can be made sufficiently high to directly vaporize the stained substance. For example, in the case where streptococcus faecalis is stained with Black Shade No. 4625 and irradiated by an Nd:YAG laser, this effect can be achieved with an energy density of the order of 10 $J/cm^2$.

To improve efficiency in accordance with tile present invention, the dentifrice transmits an optimum amount of electromagnetic radiation therethrough. In an embodiment of the invention, an optimum amount of transmission through the dentifrice comprises transmitting electromagnetic radiation at wavelengths and intensities thereof to facilitate reaction of the photosensitive agent, and substantially no additional electromagnetic radiation beyond that. Embodiments of the invention have the photosensitive agents dispersed throughout the dentifrice. During brushing, the dentifrice is dispersed in varying thicknesses over the target surface, which comprises the teeth and gums. To be effective, the electromagnetic radiation should penetrate through the dentifrice's varying thickness, so that significant portions of the photosensitive agent throughout the varying thicknesses are irradiated and react. For this to occur, the dentifrice transmits the radiation through the varying thicknesses, thereby enabling the significant portions of the dispersed photosensitive agent throughout the dentifrice to substantially absorb the radiation and react.

In modified embodiments of the invention, the dentifrice is clear, translucent, tinted, opaque, or a combination thereof. The term "clear" shall be understood to mean visually colorless and transparent. In one embodiment of the invention, the dentifrice is a clear gel comprising at least about 1.5 percent hydrogen peroxide and a clear base. In one exemplary embodiment, the base comprises water, hydrogen peroxide, poloxamer 407, glycerine, flavor and sodium saccharin. In another exemplary embodiment, the base comprises fluoride (a well-known anti-caries agent), hydrogen peroxide, and hydrated silica. The clear gel maximizes transmission of radiation therethrough, to thereby maximize an interaction of the clear gel with the radiation throughout the thickness of the clear gel.

Other agents or bleaching agents may be used in the dentifrice exclusively, or in combination with, hydrogen peroxide, in accordance with modified embodiments of the invention.

In further modified embodiments of the invention, the container may comprise compartments which hold a first portion of the dentifrice in one compartment and a second portion of the dentifrice in the other compartment (not shown). The separation of the dentifrice portions may be to prevent components in the separate portions from reacting prior to use. For example, a first portion comprising baking soda can be separated from a second portion comprising hydrogen peroxide.

In accordance with one embodiment, the active ingredient or ingredients of the dentifrice are engineered to remain relatively stable until the dentifrice is disposed on the tooth. In an embodiment where the dentifrice comprises peroxide, for example, the dentifrice is engineered to hold the peroxide in a relatively stable condition both while in the tube and while initially on the toothbrush.

In addition to engineering the dentifrice to remain stable until placed on the tooth and agitated, a method of the invention comprises a step of instructing the user to leave the source of the toothbrush in an off mode until the toothbrush and dentifrice are placed on the teeth. The user follows the instructions and inserts the toothbrush, with the dentifrice thereon and with the source in an off mode, into the mouth and onto the teeth of the user. Subsequently, the user places the source into an on mode to thereby initiate the emission of radiation from the toothbrush into the dentifrice. The user can then move the bristles of the toothbrush on the teeth to agitate and further activate the active the ingredient or ingredients of the dentifrice. In selected embodiments, the mere placement of the dentifrice on a tooth, with or without agitation, initiates activation of the ingredient or ingredients of the dentifrice. For example, a stain comprising iron, disposed on a tooth, can help to activate the peroxide of a dentifrice when the dentifrice is placed into contact with the stain on the tooth. In this example, the additional irradiation of the dentifrice can enhance the activation. In other embodiments of the above examples, the bristles of the toothbrush are placed only into close proximity with the teeth.

In still other embodiments of the invention, the dentifrice may comprise abrasives. The abrasives may be visible, an example of which is disclosed in U.S. Pat. No. 3,935,306 entitled TOOTHPASTE FORMULATIONS, which is incorporated herein by reference. The abrasives may be clear, an example of which is disclosed in U.S. Pat. No. 3,864,470 entitled VISUALLY CLEAR TOOTHPASTE CONTAINING SYNTHETIC PRECIPITATED HYDRATED SILICA, which is incorporated herein by reference. Clear abrasive particles enhance the transmissibility of the dentifrice, as compared to opaque abrasive particles.

In an embodiment of the invention, the electromagnetic radiation emitted from the toothbrush 1 is substantially free of ultraviolet radiation. Ultraviolet radiation is a relatively high energy wavelength range, compared to visible and infrared wavelengths. Under some circumstances, directing ultraviolet radiation into the mouth may result in cellular damage. Further, as the ultraviolet radiation is higher energy, the toothbrush 1 may consume less energy during operation as it does not emit the higher energy ultraviolet wavelengths.

In an embodiment of the invention, the dentifrice and the toothbrush 1 are tuned to be efficient. The dentifrice is formulated with a photosensitive agent. The dentifrice is then tested, using techniques known to those skilled in the art, to determine wide-range reactive electromagnetic radiation wavelengths that cause the photosensitive agents to react. The toothbrush 1 is then designed such that it emits at least a portion of the wide-range electromagnetic radiation wavelengths. Other embodiments of the invention may comprise a toothbrush that emits electromagnetic radiation wavelengths consisting essentially of non-ultraviolet radiation, or, consisting essentially of wavelengths within a range of 300 to 750 nanometers.

Other embodiments of the invention comprise a toothbrush that emits electromagnetic radiation within the infrared or near-infrared region. Compounds can be selected to react with this light exclusively or in addition to other wavelengths. The radiation from the source may comprise a single wavelength in the infrared or near-infrared region, or may comprise a plurality of wavelengths in the infrared or near-infrared region. In one embodiment, the infrared or near-infrared region is selected to comprise a range of wavelengths from about 700 nm to about 990 nm. In another embodiment, the infrared or near-infrared region is selected to comprise visible light, as well, for a combined range of wavelengths from about 300 nm to about 990 nm, or to about 1 µm.

Other embodiments of the invention may comprise determining a narrow-range of electromagnetic radiation wavelengths, wherein the photosensitive agent has a relatively high reaction rate when exposed to the narrow-range reactive electromagnetic radiation wavelengths compared to an average reaction rate when the photosensitive agent is exposed to the wide-range reactive electromagnetic radiation wavelengths. The toothbrush 1 is designed to provide electromagnetic radiation, which is substantially in the narrow-range reactive electromagnetic radiation wavelengths.

In another embodiment of the invention, the dentifrice and the toothbrush 1 are tuned to be efficient in a different process than described above. The dentifrice is formulated to react to the electromagnetic radiation emitted from the toothbrush 1. Embodiments of the invention may have a toothbrush that emits electromagnetic radiation wavelengths consisting essentially of non-ultraviolet radiation or consisting essentially of wavelengths within a range of 300 to 750 nanometers.

While the description above refers to particular embodiments of the present invention, it will be understood that many modifications may be made without departing from the spirit thereof. For example, embodiments of the invention may have a toothbrush emitting either polychromatic or monochromatic electromagnetic radiation. Additionally, the electromagnetic radiation may be coherent or non-coherent. Further, aspects of the invention may have combinations of the above-described embodiments although these combinations may not be explicitly described. The accompanying claims are intended to cover such embodiments as would fall within the true scope and spirit of the present invention.

The invention claimed is:

1. A cleaning system for teeth, comprising:
a toothbrush having a cleaning surface, the toothbrush comprising a source of electromagnetic radiation configured to direct polychromatic electromagnetic radiation toward the cleaning surface, wherein the polychromatic electromagnetic radiation consists essentially of wavelengths from 300 to 750 nanometers, wherein an output configuration of the source of electromagnetic energy is relatively low such that electromagnetic radiation can be emitted toward the cleaning surface of the toothbrush during brushing to enhance cleaning of the teeth when used in combination with a dentifrice; and
a dentifrice comprising a photosensitive agent dispersed throughout the dentifrice and including a whitening peroxy compound, the dentifrice being adapted to be dispersed over a target surface and to transmit the polychromatic electromagnetic radiation, whereby during use a significant portion of the dispersed photosensitive agent over the target surface receives the polychromatic electromagnetic radiation, thus enabling the significant portion of the dispersed photosensitive agent to react.

2. The teeth cleaning system of claim 1, wherein:
the dentifrice comprises a dispersed photosensitive agent that reacts substantially only to electromagnetic radiation within a predetermined range of wavelengths; and
the electromagnetic radiation is bound to wavelengths that are substantially within the predetermined range.

3. The teeth cleaning system of claim 1, wherein the dentifrice comprises a clear gel that allows the polychromatic electromagnetic radiation to reach the dispersed photosensitive agent throughout the clear gel.

4. The teeth cleaning system of claim 1, wherein the dentifrice comprises an anti-caries agent.

5. The teeth cleaning system of claim 4, wherein the polychromatic electromagnetic radiation reaching the anti-caries agent produces an anti-caries effect.

6. The teeth cleaning system of claim 1, wherein the dentifrice comprises a clear gel that maximizes transmission of the polychromatic electromagnetic radiation therethrough, to thereby maximize an interaction of the dispersed photosensitive agent with the polychromatic electromagnetic radiation throughout a thickness of the clear gel.

7. The teeth cleaning system of claim 1, wherein the dentifrice comprises clear abrasive particles.

8. The teeth cleaning system of claim 1, wherein the dentifrice comprises fluoride.

9. The teeth cleaning system of claim 8, wherein the dentifrice comprises a clear gel that allows the polychromatic electromagnetic radiation to reach the fluoride throughout the clear gel.

10. The teeth cleaning system of claim 1, wherein the polychromatic electromagnetic radiation is emitted from a light emitting diode.

11. The teeth cleaning system of claim 1, wherein the toothbrush emits electromagnetic radiation wavelengths consisting essentially of non-ultraviolet radiation during brushing.

12. The teeth cleaning system of claim 11, wherein the dentifrice comprises an anti-caries agent.

13. The teeth cleaning system of claim 12, wherein the anti-caries agent comprises fluoride.

14. The teeth cleaning system of claim 12, wherein the dentifrice comprises a clear gel that maximizes transmission of the polychromatic electromagnetic radiation to allow the polychromatic electromagnetic radiation to reach the anti-caries agent throughout the clear gel and to produce an anti-caries effect.

15. The teeth cleaning system of claim 11, wherein the dentifrice comprises is clear component that operates to facilitate a maximal transmission of the polychromatic electromagnetic radiation through the dentifrice to allow the polychromatic electromagnetic radiation to reach the cleaning or lightening photosensitive agent throughout the clear gel.

16. The teeth cleaning system of claim 11, wherein the dentifrice is a clear gel.

17. The teeth cleaning system of claim 11, wherein the dentifrice comprises clear abrasive particles.

18. The teeth cleaning system of claim 11, wherein the dentifrice comprises a clear gel that maximizes transmission of the polychromatic electromagnetic radiation therethrough, to thereby maximize an interaction of the cleaning or lightening photosensitive agent with the polychromatic electromagnetic radiation throughout a thickness of the clear gel.

19. The teeth cleaning system of claim 11, wherein the polychromatic electromagnetic radiation is emitted from a light emitting diode.

20. A cleaning system for teeth, comprising:
a toothbrush having a cleaning surface, the toothbrush comprising a source of electromagnetic radiation configured to direct polychromatic electromagnetic radiation toward the cleaning surface, wherein the polychromatic electromagnetic radiation consists essentially of wavelengths from 300 to 750 nanometers, wherein an output configuration of the source of electromagnetic energy is relatively low such that electromagnetic radiation can be emitted toward the cleaning surface of the toothbrush during brushing to enhance cleaning of the teeth when used in combination with a dentifrice; and
a dentifrice comprising a photosensitive agent dispersed throughout the dentifrice, the dentifrice comprising about 1.5% peroxide and being adapted to be dispersed over a target surface and to transmit the polychromatic electromagnetic radiation, whereby during use a significant portion of the dispersed photosensitive agent over the target surface receives the polychromatic electromagnetic radiation, thus enabling the significant portion of the dispersed photosensitive agent to react.

21. The system of claim 20, wherein the source of electromagnetic radiation comprises a continuous wave source of electromagnetic radiation.

22. The system of claim 20, wherein the toothbrush comprises bristles and is constructed to direct polychromatic electromagnetic radiation through the bristles toward the cleaning surface.

23. The system of claim 20, wherein the toothbrush comprises bristles and is constructed to direct polychromatic electromagnetic radiation around the bristles toward the cleaning surface.

24. The system of claim 20, wherein the dentifrice is a clear gel.

25. The system of claim 20, wherein the dentifrice comprises an anti-caries agent.

26. The system of claim 25, wherein the source of electromagnetic radiation comprises a continuous wave source of electromagnetic radiation.

27. The system of claim 25, wherein the toothbrush comprises bristles and is constructed to direct the polychromatic electromagnetic radiation through the bristles toward the cleaning surface.

28. The system of claim 25, wherein the toothbrush comprises bristles and is constructed to direct the polychromatic electromagnetic radiation around the bristles toward the cleaning surface.

29. The system of claim 28, wherein the dentifrice is a clear gel.

30. The system of claim 25, wherein the dentifrice comprises a clear gel that maximizes transmission of the polychromatic electromagnetic radiation therethrough, to thereby maximize an interaction of the clear gel with the polychromatic electromagnetic radiation throughout a thickness of the clear gel.

31. The system of claim 25, wherein the anti-caries agent comprises fluoride.

32. The system of claim 31, wherein the dentifrice comprises a clear gel that maximizes transmission of the polychromatic electromagnetic radiation therethrough, to thereby maximize an interaction of the clear gel with the polychromatic electromagnetic radiation throughout a thickness of the clear gel.

33. The system of claim 31, wherein the dentifrice comprises a clear gel that allows the polychromatic electromagnetic radiation to reach the anti-caries agent throughout the clear gel.

34. The system of claim 33, wherein the polychromatic electromagnetic radiation reaching the anti-caries agent produces an anti-caries effect.

35. The system of claim 25, wherein the dentifrice comprises a clear gel that allows the polychromatic electromagnetic radiation to reach the anti-caries agent throughout the clear gel.

36. The system of claim 35, wherein the polychromatic electromagnetic radiation reaches the anti-caries agent to produce an anti-caries effect.

37. A cleaning system for teeth, comprising:
a toothbrush having a cleaning surface, the toothbrush comprising a source of electromagnetic radiation configured to direct polychromatic electromagnetic radiation toward the cleaning surface, wherein the polychromatic electromagnetic radiation consists essentially of wavelengths from 300 to 750 nanometers, wherein an output configuration of the source of electromagnetic energy is relatively low such that polychromatic electromagnetic radiation can be emitted toward the cleaning surface of the toothbrush during brushing to enhance cleaning of the teeth when used in combination with a dentifrice; and a dentifrice comprising a photosensitive agent dispersed throughout the dentifrice and including whitening hydrogen peroxide or carbamide peroxide, the dentifrice being adapted to be dispersed over a target surface and to transmit the polychromatic electromagnetic radiation, whereby during use a significant portion of the dispersed photosensitive agent over the target surface receives the polychromatic electromagnetic radiation, thus enabling the significant portion of the dispersed photosensitive agent to react.

38. The system of claim 37, wherein the dentifrice is hydrogen peroxide or carbamide peroxide.

39. The system of claim 37, wherein the dentifrice is a peroxy compound.

40. The system of claim 37, wherein the dentifrice comprises about 1.5% peroxide.

41. The system of claim 37, wherein the source of electromagnetic radiation comprises a continuous wave source of electromagnetic radiation.

42. The system of claim 37, wherein the source of electromagnetic radiation comprises a light emitting diode.

43. The system of claim 42, wherein the source of electromagnetic radiation comprises a continuous wave source of electromagnetic radiation.

44. The system of claim 37, wherein the toothbrush comprises bristles and is constructed to direct the polychromatic electromagnetic radiation through the bristles toward the cleaning surface.

45. The system of claim 37, wherein the toothbrush comprises bristles and is constructed to direct the polychromatic electromagnetic radiation around the bristles toward the cleaning surface.

46. The system of claim 37, wherein the dentifrice is a clear gel.

47. The system of claim 46, wherein the source of electromagnetic radiation comprises a continuous wave source of electromagnetic radiation.

48. The system of claim 46, wherein the source of electromagnetic radiation comprises a light emitting diode.

49. The system of claim 46, wherein the toothbrush comprises bristles and is constructed to direct the polychromatic electromagnetic radiation through the bristles toward the cleaning surface.

50. The system of claim 46, wherein the toothbrush comprises bristles and is constructed to direct the polychromatic electromagnetic radiation around the bristles toward the cleaning surface.

51. The system of claim 46, wherein the dentifrice comprises about 1.5% peroxide.

52. The system of claim 37, wherein the dentifrice comprises an anti-caries agent.

53. The system of claim 52, wherein the dentifrice comprises a clear gel that maximizes transmission of the polychromatic electromagnetic radiation therethrough, to thereby maximize an interaction of the clear gel with the polychromatic electromagnetic radiation throughout a thickness of the clear gel.

54. The system of claim 52, wherein the anti-caries agent comprises fluoride.

55. The system of claim 54, wherein the dentifrice comprises a clear gel that maximizes transmission of the polychromatic electromagnetic radiation therethrough, to thereby maximize an interaction of the clear gel with the polychromatic electromagnetic radiation throughout a thickness of the clear gel.

56. The system of claim 54, wherein the dentifrice comprises a clear gel that allows the polychromatic electromagnetic radiation to reach the anti-caries agent throughout the clear gel.

57. The system of claim 56, wherein the polychromatic electromagnetic radiation reaching the anti-caries agent produces an anti-caries effect.

58. The system of claim 52, wherein the dentifrice comprises a clear gel that allows the polychromatic electromagnetic radiation to reach the anti-caries agent throughout the clear gel.

59. The system of claim 58, wherein the polychromatic electromagnetic radiation reaches the anti-caries agent to produce an anti-caries effect.

60. A cleaning system for teeth, comprising:
a toothbrush having a cleaning surface, the toothbrush comprising a source of electromagnetic radiation configured to direct polychromatic electromagnetic radiation toward the cleaning surface, wherein the polychromatic electromagnetic radiation consists essentially of wavelengths from 300 to 750 nanometers, wherein an output configuration of the source of electromagnetic energy is relatively low such that electromagnetic radiation can be emitted toward the cleaning surface of the toothbrush during brushing to enhance cleaning of the teeth when used in combination with a dentifrice; and
a dentifrice comprising a photosensitive agent dispersed throughout the dentifrice and including one or more salt compounds, the dentifrice being adapted to be dispersed over a target surface and to transmit the polychromatic electromagnetic radiation, whereby during use a significant portion of the dispersed photosensitive agent over the target surface receives the polychromatic electromagnetic radiation, thus enabling the significant portion of the dispersed photosensitive agent to react.

61. The system of claim 60, wherein the dentifrice is aqueous and at least a portion of the one or more salt compounds is dissolved in the dentifrice.

62. The system of claim 61, wherein the electromagnetic radiation is continuous-wave electromagnetic radiation.

63. The system of claim 60, wherein the electromagnetic radiation is continuous-wave electromagnetic radiation.

64. The system of claim 60, wherein the electromagnetic radiation is emitted from a light emitting diode.

65. The system of claim 60, wherein the toothbrush comprises bristles and is constructed to direct electromagnetic radiation through the bristles.

66. The system of claim 60, wherein the toothbrush comprises bristles and is constructed to direct electromagnetic radiation round the bristles.

67. The system of claim 60, wherein the dentifrice is a clear gel.

68. The system of claim 60, wherein the dentifrice comprises about 1.5% peroxide.

69. The system of claim 60, wherein the dentifrice comprises an anti-caries agent.

70. The system of claim 69, wherein the dentifrice comprises a clear gel that maximizes transmission of electromagnetic radiation therethrough, to thereby maximize an interaction of the clear gel with the electromagnetic radiation throughout a thickness of the clear gel.

71. The system of claim 69, wherein the anti-caries agent comprises fluoride.

72. The system of claim 71, wherein the dentifrice comprises a clear gel that maximizes transmission of electromagnetic radiation therethrough, to thereby maximize an interaction of the clear gel with the electromagnetic radiation throughout a thickness of the clear gel.

73. The system of claim 71, wherein the dentifrice comprises a clear gel that maximizes transmission of electromagnetic radiation to allow the electromagnetic radiation to reach the anti-caries agent throughout the clear gel.

74. The system of claim 73, wherein the electromagnetic radiation reaching the anti-caries agent produces an anti-caries effect.

75. The system of claim 69, wherein the dentifrice comprises a clear gel that maximizes transmission of electromagnetic radiation to allow the electromagnetic radiation to reach the anti-caries agent throughout the clear gel.

76. The system of claim 75, wherein the electromagnetic radiation reaching the anti-caries agent produces an anti-caries effect.

77. A cleaning system for teeth, comprising:
a toothbrush having a cleaning surface and a source of electromagnetic radiation constructed to direct electromagnetic radiation toward the cleaning surface, wherein the electromagnetic radiation is at least substantially free of ultraviolet radiation; and
a dentifrice comprising a photosensitive agent, which is dispersed throughout the dentifrice, wherein during use the dentifrice is dispersed over a target surface and the dentifrice has a transparency sufficient to transmit the electromagnetic radiation, whereby a significant portion of the dispersed photosensitive agent over the target surface receives the electromagnetic radiation during use of the system, thus enabling the significant portion of the dispersed photosensitive agent to react, wherein the photosensitive agent comprises one or more salt compounds.

78. The cleaning system of claim 77, wherein the dentifrice is aqueous and at least a portion of the one or more salt compounds is dissolved in the dentifrice.

79. The cleaning system of claim 77, wherein the source of electromagnetic radiation comprises a light emitting diode source of polychromatic electromagnetic radiation.

80. The cleaning system of claim 77, wherein the dentifrice comprises clear abrasive particles.

81. The cleaning system of claim 80, wherein the electromagnetic radiation is continuous-wave electromagnetic radiation.

82. The cleaning system of claim 80, wherein the electromagnetic radiation is polychromatic electromagnetic radiation.

83. The cleaning system of claim 80, wherein electromagnetic radiation is monochromatic electromagnetic radiation.

84. The cleaning system of claim 77, wherein the electromagnetic radiation is continuous-wave electromagnetic radiation.

85. The cleaning system of claim 84, wherein the electromagnetic radiation is emitted from a light emitting diode.

86. The cleaning system of claim 85, wherein: the source of electromagnetic radiation comprises a source of polychromatic electromagnetic radiation.

87. The cleaning system of claim 77, wherein the toothbrush comprises bristles and is constructed to direct electromagnetic radiation through the bristles toward the cleaning surface.

88. The cleaning system of claim 77, wherein the toothbrush comprises bristles and is constructed to direct electromagnetic radiation around the bristles toward the cleaning surface.

89. The cleaning system of claim 77, wherein the dentifrice is a clear gel.

90. The cleaning system of claim 77, wherein the source of electromagnetic radiation comprises a light emitting diode.

91. The cleaning system of claim 90, wherein the electromagnetic radiation consists essentially of a band of wavelengths from 300 to 750 nanometers.

92. The cleaning system of claim 77, wherein the dentifrice comprises an anti-caries agent.

93. The cleaning system of claim 92, wherein the anti-caries agent comprises fluoride.

94. The cleaning system of claim 77, wherein the dentifrice comprises a clear gel that maximizes transmission of electromagnetic radiation therethrough and maximizes an interaction of the photosensitive agent with the electromagnetic radiation throughout a thickness of the clear gel.

95. The cleaning system of claim 94, wherein the dentifrice comprises clear abrasive particles.

96. The cleaning system of claim 94, wherein the photosensitive agent comprises hydrogen peroxide or carbamide peroxide.

97. The cleaning system of claim 94, wherein the photosensitive agent comprises a peroxy compound.

98. The cleaning system of claim 94, wherein the source of electromagnetic radiation comprises a source of polychromatic electromagnetic radiation.

99. The cleaning system of claim 77, wherein the source of electromagnetic radiation comprises a source of monochromatic electromagnetic radiation.

100. The cleaning system of claim 77, wherein the electromagnetic radiation consists essentially of a band of wavelengths from 300 to 750 nanometers.

101. The cleaning system of claim 77, wherein the dentifrice comprises a whitening compound.

102. A teeth cleaning system, comprising:
  a. a dentifrice comprising a photosensitive agent that reacts substantially only to electromagnetic radiation within a predetermined range wherein:
    i. the photosensitive agent is dispersed throughout the dentifrice;
    ii. the dentifrice is dispersed over a target surface during use of the system; and
    iii. the dentifrice has a transparency sufficient to transmit the electromagnetic radiation, whereby a significant portion of the dispersed photosensitive agent over the target surface receives the electromagnetic radiation during use of the system, thus enabling the significant portion of the dispersed photosensitive agent to react; and
  b. a toothbrush having a cleaning surface, the toothbrush comprising a source of electromagnetic radiation constructed to direct electromagnetic radiation toward the cleaning surface, wherein the electromagnetic radiation is bound to wavelengths that are substantially within the predetermined range, wherein the photosensitive agent comprises one or more salt compounds.

103. The cleaning system of claim 102, wherein the dentifrice is aqueous and at least a portion of the one or more salt compounds is dissolved in the dentifrice.

104. The cleaning system of claim 102, wherein the source of electromagnetic radiation comprises a light emitting diode.

105. The cleaning system of claim 104, wherein the dentifrice comprises an anti-caries agent.

106. The cleaning system of claim 105, wherein the electromagnetic radiation is continuous-wave electromagnetic radiation.

107. The cleaning system of claim 105, wherein the electromagnetic radiation is polychromatic electromagnetic radiation.

108. The cleaning system of claim 107, wherein the electromagnetic radiation is continuous-wave electromagnetic radiation.

109. The cleaning system of claim 105, wherein the electromagnetic radiation is monochromatic electromagnetic radiation.

110. The cleaning system of claim 105, wherein the electromagnetic radiation is continuous-wave electromagnetic radiation.

111. The cleaning system of claim 110, wherein the source of electromagnetic radiation comprises a source of polychromatic electromagnetic radiation.

112. The cleaning system of claim 105, wherein the toothbrush comprises bristles and is constructed to direct electromagnetic radiation through the bristles toward the cleaning surface.

113. The cleaning system of claim 105, wherein the toothbrush comprises bristles and is constructed to direct electromagnetic radiation around the bristles toward the cleaning surface.

114. The cleaning system of claim 105, wherein the dentifrice comprises a clear gel that maximizes transmission of electromagnetic radiation therethrough, to thereby maximize an interaction of the clear gel with the electromagnetic radiation throughout a thickness of the clear gel.

115. The cleaning system of claim 105, wherein the anti-caries agent comprises fluoride.

116. The cleaning system of claim 115, wherein the dentifrice comprises a clear gel that maximizes transmission of electromagnetic radiation therethrough, to thereby maximize an interaction of the clear gel with the electromagnetic radiation throughout a thickness of the clear gel.

117. The cleaning system of claim 115, wherein the dentifrice comprises a clear gel that allows the electromagnetic radiation to reach the anti-caries agent throughout the clear gel.

118. The cleaning system of claim 117, wherein the electromagnetic radiation reaches the anti-caries agent to produce an anti-caries effect.

119. The cleaning system of claim 105, wherein the dentifrice comprises a clear gel that allows the electromagnetic radiation to reach the anti-caries agent throughout the clear gel.

120. The cleaning system of claim 119, wherein the electromagnetic radiation reaching the anti-caries agent produces an anti-caries effect.

121. The cleaning system of claim 104, wherein the source of electromagnetic radiation comprises a source of polychromatic electromagnetic radiation.

122. The cleaning system of claim 102, wherein the dentifrice comprises an anti-caries agent.

123. The cleaning system of claim 122, wherein the anti-caries agent comprises fluoride.

124. The cleaning system of claim 102, wherein the dentifrice is a clear gel that maximizes transmission of electromagnetic radiation therethrough, to thereby maximize an interaction of the clear gel with the electromagnetic radiation throughout a thickness of the clear gel.

125. The cleaning system of claim 102, wherein the photosensitive agent comprises a whitening compound.

126. The cleaning system of claim 125, wherein the whitening compound is hydrogen peroxide or carbamide peroxide.

127. The cleaning system of claim 125, wherein the whitening compound is a peroxy compound.

128. The cleaning system of claim 102, wherein the source of electromagnetic radiation comprises a source of polychromatic electromagnetic radiation.

129. The cleaning system of claim 128, wherein the electromagnetic radiation consists essentially of a band of wavelengths from 300 to 750 nanometers.

130. The cleaning system of claim 128, wherein the source of polychromatic electromagnetic radiation comprises a light emitting diode.

131. The cleaning system of claim 102, wherein the source of electromagnetic radiation comprises a source of monochromatic electromagnetic radiation.

132. The cleaning system of claim 102, wherein the dentifrice comprises clear abrasive particles.

133. A cleaning system for teeth, comprising:
- a toothbrush having a cleaning surface, the toothbrush comprising a source of electromagnetic radiation configured to direct electromagnetic radiation toward the cleaning surface, wherein an output configuration of the source of electromagnetic energy is relatively low such that electromagnetic radiation can be emitted toward the cleaning surface of the toothbrush during brushing to enhance cleaning of the teeth when used in combination with a dentifrice; and
- a dentifrice comprising a photosensitive agent which includes one or more salt compounds and which is dispersed throughout the dentifrice, the dentifrice being adapted to be dispersed at a thickness over the teeth and to maximize a transmission of the electromagnetic radiation therethrough, whereby during use an interaction of a significant portion of the dispersed photosensitive agent with the electromagnetic radiation is maximized throughout the thickness thus enabling the significant portion of the dispersed photosensitive agent to react.

134. The cleaning system of claim 133, wherein the photosensitive agent comprises a whitening compound.

135. The cleaning system of claim 134, wherein the whitening compound is a peroxy compound.

136. The cleaning system of claim 134, wherein the whitening compound is hydrogen peroxide or carbamide peroxide.

137. The cleaning system of claim 134, wherein the photosensitive agent comprises a whitening compound that imparts a whitening or an enhanced whitening effect onto the teeth upon receipt of the electromagnetic radiation.

138. The cleaning system of claim 133, wherein the dentifrice comprises an anti-caries agent.

139. The cleaning system of claim 138, wherein the electromagnetic radiation reaches the anti-caries agent to produce an anti-caries effect.

140. The cleaning system of claim 138, wherein the anti-caries agent comprises fluoride.

141. The cleaning system of claim 133, wherein the dentifrice is a clear gel.

142. The cleaning system of claim 141, wherein the dentifrice comprises clear abrasive particles.

143. The cleaning system of claim 133, wherein the dentifrice comprises a clear gel that maximizes transmission of electromagnetic radiation therethrough, to thereby maximize an interaction of the clear gel with the electromagnetic radiation throughout a thickness of the clear gel.

144. The cleaning system of claim 133, wherein the dentifrice comprises a clear gel that allows the electromagnetic radiation to reach the photosensitive agent throughout the clear gel.

145. The cleaning system of claim 133, wherein the dentifrice comprises clear abrasive particles.

146. The cleaning system of claim 133, wherein the electromagnetic radiation comprises polychromatic electromagnetic radiation.

147. The cleaning system of claim 146, wherein the polychromatic electromagnetic radiation consists essentially of a band of wavelengths from 300 to 750 nanometers.

* * * * *